United States Patent [19]

Kano et al.

[11] Patent Number: 4,556,641

[45] Date of Patent: Dec. 3, 1985

[54] METHOD OF JUDGING A PARTICLE AGGLUTINATION REACTION AND A REACTION VESSEL FOR USE IN THE METHOD

[75] Inventors: Tokio Kano, Kunitachi; Akira Tamagawa, Hino, both of Japan

[73] Assignee: Olympus Optical Co., Ltd., Tokyo, Japan

[21] Appl. No.: 437,692

[22] Filed: Oct. 29, 1982

[30] Foreign Application Priority Data

Nov. 2, 1981 [JP] Japan ............................ 56-176250

[51] Int. Cl.$^4$ ...................... G01N 21/82; G01N 33/54
[52] U.S. Cl. ...................................... 436/165; 422/73; 422/102; 436/533; 436/534; 436/805
[58] Field of Search .................. 436/43, 809, 805, 69, 436/165, 533, 534; 422/73, 102; 356/343; 73/64.1

[56] References Cited

U.S. PATENT DOCUMENTS

| | | | |
|---|---|---|---|
| 3,520,609 | 7/1970 | Lion | 422/73 |
| 3,883,308 | 5/1975 | Matte | 436/809 |
| 4,303,616 | 12/1981 | Kano et al. | 422/73 |
| 4,341,471 | 7/1982 | Hogg et al. | 356/343 |

FOREIGN PATENT DOCUMENTS 56-2560  1/1981  Japan ................................. 422/73

Primary Examiner—David L. Lacey
Assistant Examiner—Robert J. Hill, Jr.
Attorney, Agent, or Firm—Parkhurst & Oliff

[57] ABSTRACT

A reaction vessel having a ring-shaped flat bottom portion and a conically inclined bottom portion is used to detect a particle agglutination reaction. Image of particle patterns formed on the flat bottom portion, middle and lowermost portion of the inclined bottom portion are separately detected by first, second and third light receiving elements to produce first, second and third signals. When the first signal is within a predetermined standard range, the particle agglutination reaction is judged by comparing a difference between the second and third signals with a predetermined upper and lower standard values. Contrary to this, when the first signal is beyond the predetermined range, the judgement for the agglutination reaction is not effected.

9 Claims, 3 Drawing Figures

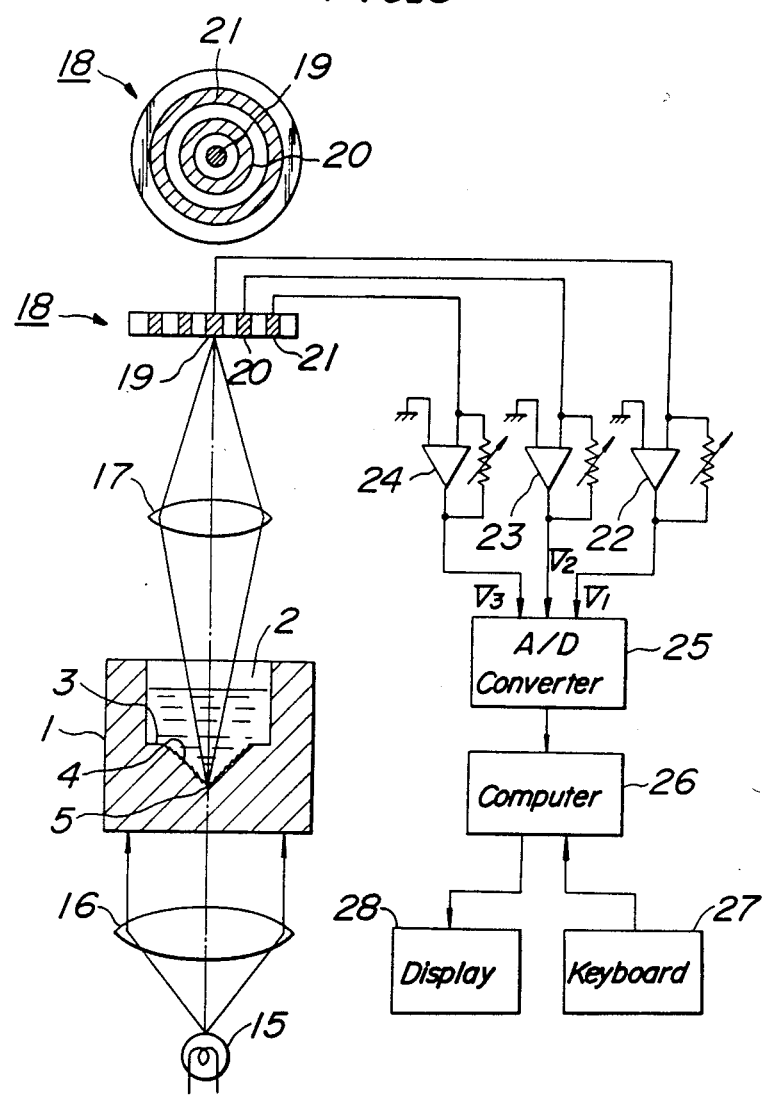

METHOD OF JUDGING A PARTICLE AGGLUTINATION REACTION AND A REACTION VESSEL FOR USE IN THE METHOD

BACKGROUND OF THE INVENTION

The present invention generally relates to an immunological agglutination analysis and more particularly to a technique for testing or judging the existence of particular antigens or antibodies due to a particle agglutination reaction.

Heretofore, there have been proposed various types of such immunological agglutination judging methods for determining the blood types and various kinds of antigens and antibodies by detecting photoelectrically an agglutinated particle pattern or a non-agglutinated particle pattern formed by descending particles on a conically inclined bottom surface of a reaction vessel, while the reaction vessel is maintained substantially stationary. It has been further proposed to provide a number of reaction vessels each having a conical bottom surface in a matrix form in a base plate to constitute a microplate. In such an immunological agglutination testing method using the reaction vessel having the inclined bottom surface, when there is the agglutination reaction, the agglutinated particles are deposited on the inclined surface just like snow to form an uniformly deposited pattern, while in case of the non-agglutination reaction, the particles roll down along the inclined surface and are collected at the lowermost center portion, i.e. an apex of the cone to form a collected pattern. In one known method for detecting photoelectrically the uniformly deposited pattern and the collected pattern to distinguish therebetween, a light flux transmitted through the lowermost portion of the inclined surface is received by a light receiving element to produce a photoelectrically converted signal and then this signal is compared with a predetermined reference level to detect the existence or non-existence of the particle agglutination reaction. In another known method, an image of the particle pattern on the conical bottom surface is formed on an image plane on which two light receiving elements are arranged in such a manner that the first element can selectively receive an image on the lowermost portion of the conical bottom surface and the second element can exclusively receive an image on a portion of the inclined bottom surface surrounding said lowermost portion, and a difference between output signals of these elements is compared with a predetermined reference level to detect the existence of the particle agglutination reaction.

In the known methods, when the concentration of a particle suspension and an amount of the particle suspension delivered into the reaction vessel are varied, the outputs of the light detectors are also varied and thus, an accurate detection can not be effected. For instance, in case of determining the blood types, a sample of whole blood is first centrifuged to form a blood cell sediment and a given amount of the sedimented blood cells is sucked and delivered into the reaction vessel. In this case, the degree of sedimentation of blood cells during centrifugation might be affected by a variation of various conditions of the centrifuge, mechanical shock and vibration to which the sedimented blood cells are subjected after centrifugation and differences in viscosity and specific gravity of blood cells and blood plasma. Therefore, even if a predetermined amount of blood cell sediment is delivered, a variation in the amount and/or concentration of delivered blood cells might be produced. Further, such a variation might be produced due to a fluctuation of the delivery mechanism.

When the particle concentration and/or the amount of the delivered particle sample are varied, in the former method, the uniformly deposited particle pattern might be erroneously judged as the collected particle pattern when the particle concentration is too high, because the amount of light flux transmitted through the lowermost central portion of the conical bottom surface becomes too small, while the collected pattern might be judged as the uniformly deposited pattern when the particle concentration is too low, because the amount of light flux transmitted through the lowermost central portion is increased. Further, in the latter known method, the uniformly deposited pattern might be erroneously determined as a halfly deposited pattern which is produced by particles having a weak agglutination reaction, when the particle concentration is too high, because a part of particles which could not be fully agglutinated fall down into the lowermost portion. Contrary to this, when the particle concentration is too low, the halfly deposited pattern might be misjudged as the uniformly deposited pattern, and the collected pattern might be erroneously judged as the uniformly deposited pattern, because the amount of particles deposited at the lowermost portion becomes too small. Moreover, when the particle concentration becomes extremely small, even in case of the non-agglutination reaction, since an amount of particles collected in the lowermost portion becomes very small, the collected pattern could hardly be distinguished from the uniformly deposited pattern.

SUMMARY OF THE INVENTION

The present invention has for its object to provide a novel and useful method for judging a particle agglutination reaction in which the particle patterns can be clearly distinguished from each other even if a particle amount and/or a particle concentration of a test liquid delivered into a reaction vessel are varied to a great extent.

According to the invention, a method of judging a particle agglutination reaction by detecting a particle pattern formed on an inclined bottom surface of a reaction vessel for containing a test liquid comprises
  detecting photoelectrically an amount and/or a concentration of particles contained in the test liquid to produce a first signal;
  detecting photoelectrically a particle pattern formed by particles descending upon the inclined bottom surface of the reaction vessel to produce a second signal; and
  judging the particle agglutination reaction on the basis of said first and second signals.

The present invention also relates to a novel and useful reaction vessel for use in the above mentioned particle agglutination reaction judging method.

According to the invention, a reaction vessel for use in judging a particle agglutination reaction comprises
  a main body having at least one depression for containing a test liquid;
  a flat bottom portion formed in the depression; and
  an inclined bottom portion formed in the depression; whereby said flat bottom portion serves to form a particle pattern corresponding to the particle concentration and/or particle amount and said inclined bottom portion serves to form a particle pattern corresponding to the agglutination reaction.

BRIEF DESCRIPTION OF THE DRAWINGS

FIG. 3 is a schematic view illustrating an embodiment of an apparatus for carrying out the particle agglutination judging method according to the invention.

DESCRIPTION OF THE PREFERRED EMBODIMENTS

Figure 1:
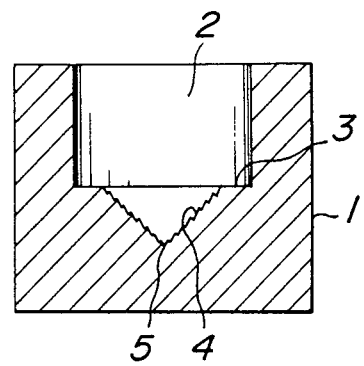
FIG. 1 is a cross sectional view showing an embodiment of the reaction vessel according to the invention.

FIG. 1 is a cross section showing an embodiment of the reaction vessel according to the invention. The reaction vessel comprises a vessel body 1 made of transparent plastics having an opening 2 through which sample and reagent are delivered into the vessel. A bottom of the vessel consists of a ring-shaped flat portion 3 integrally formed with an upright inner wall defining the opening 2, and a conically inclined portion 4 integrally formed with the flat portion 3. In the conically inclined portion 4 there are formed a number of regular steps from its upper edge to a lowermost center 5. The steps may be replaced by grooves, projections and recesses.

Figure 2:
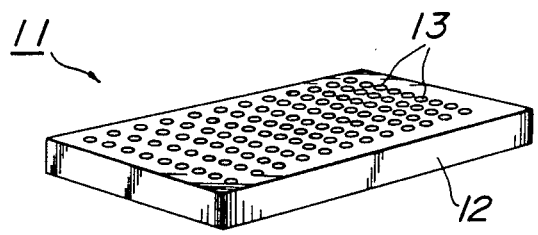
FIG. 2 is a perspective view depicting another embodiment of the reaction vessel according to the invention.

FIG. 2 is a perspective view showing another embodiment of the reaction vessel according to the invention. In this embodiment, the reaction vessel 11 comprises a base plate 12 made of transparent plastics and a number of reaction holes 13 formed in the base plate 12 in a matrix form. Each reaction hole 13 has a bottom consisting of a ring-shaped flat portion and a conically inclined portion having a number of regular steps as illustrated in FIG. 1.

In the reaction vessel according to the invention, descending particles are deposited on the flat portion 3 corresponding to a particle amount and/or a concentration of a test liquid delivered into the reaction vessel. On the inclined portion 4, at first a stable base layer of particles is formed due to the steps 5 and then, when the antigen-antibody reaction occurs, the agglutinated particles are uniformly deposited on the stable base layer to form the uniformly deposited particle pattern. Contrary to this, when the antibody-antigen reaction does not occur, the descending particles roll down along the base layer and are collected in the lowermost center 5 to form the collected particle pattern.

FIG. 3 is a schematic view illustrating an embodiment of an apparatus for effecting the particle agglutination pattern detecting method according to the invention. In this embodiment, use is made of the reaction vessel 1 shown in FIG. 1. A light flux emitted from a light source 15 is collimated by a collimator lens 16 and is made incident upon the reaction vessel 1 from its bottom. An image of a particle pattern formed on the bottom surface 3, 4 and 5 of the reaction vessel is formed by an imaging lens 17 onto a light detector 18. The light detector 18 comprises a first light receiving element 19 for receiving the image on the central portion 5, a second light receiving element 20 for receiving the image on the conically inclined portion 4 and a third light receiving element 21 for receiving the image on the flat portion 3. Therefore, these light receiving elements 19, 20 and 21 are arranged concentrically with respect to an optical axis passing through the center portion 5 of the reaction vessel. Photoelectrically converted output signals from these light receiving elements 19, 20 and 21 are supplied via pre-amplifiers 22, 23 and 24, respectively to an A-D converter 25 including a multiplexer.

The analog output signals are successively converted into digital signals which are then supplied to a computer 26 to which are also supplied from a keyboard 27 standard values as will be explained below. The computer 26 carries out given calculation with the aid of the digital signals supplied from the A/D converter 25 and the standard values supplied from the keyboard 27 to judge the particle pattern and its result is displayed on a display device 28.

Now examples of processes for judging the particle pattern will be explained.

EXAMPLE 1

In this example, a first upper and lower reference values $DR_1$ and $DR_2$ to be compared with the output signal $V_3$ supplied from the third light receiving element 21 have been previously stored in a memory of the computer 26 by means of the keyboard 27. These upper and lower reference values $DR_1$ and $DR_2$ respectively correspond to upper and lower limit values of the output signal $V_3$ which will be obtained when the particle amount and/or particle concentration of the test liquid are within a normal range. These reference values $DR_1$ and $DR_2$ can be determined experimentally.

When $V_3 > DR_1$ or $V_3 < DR_2$, it can be judged that the particle concentration and/or particle amount are out of the normal range. Then, the particle pattern determination is not effected and a suitable mark such as "ABNORMAL" is displayed on the display device 28.

When $DR_1 \geq V_3 \geq DR_2$, the particle concentration and/or particle amount can be recognized to be within the normal range. Then, the particle pattern can be judged with the aid of the output signals $V_1$ and $V_2$ supplied from the first and second light receiving elements, respectively in a similar manner as that of the known method. That is to say, at first a difference $\Delta V = V_2 - V_1$ is derived and then, the difference thus derived is compared with judgement standard upper and lower limits U.L. and L.L. (U.L.>L.L.) which have been previously stored in the computer 26 via the keyboard 27. When the particle agglutination reaction occurs, a difference in an optical density between the inclined portion 4 and the lowermost center 5 becomes very small and $\Delta V$ becomes smaller than the lower limit value L.L. Therefore, when $\Delta V < L.L.$, it is recognized that the agglutination reaction has occurred and a mark such as "+" is displayed on the display device 28. On the contrary, when the non-agglutination has occurred, the particles descending on the inclined portion 4 fall down into the center portion 5 to form the collected pattern. In this case, $\Delta V$ becomes larger than the upper limit value U.L. Therefore, when $\Delta V > U.L.$, a mark "−" is displayed on the display device 28.

When the agglutination force is weak and the halfly deposited particle pattern is formed, $U.L. \geq \Delta V \geq L.L.$ is obtained. Then, a "?" mark is displayed, because in such a case, it is difficult to effect a reliable judgement.

In the present example, the particle pattern can be judged precisely, because when the particle concentration and/or particle amount are too large or too small, the judgement is not effected. In this manner, the precision and reliability of judgement can be improved materially.

EXAMPLE 2

In this example, in the computer 26 there has been previously stored a reference value $V_{30}$ by means of the keyboard 27. This reference value $V_{30}$ corresponds to a value of the signal $V_3$ which is obtained when the particle concentration and/or particle amount are equal to predetermined standard values and can be determined experimentally. At first, a correction coefficient $\gamma = V_3/V_{30}$ is calculated in the computer 26 and then, a product of the coefficient $\gamma$ and the difference $\Delta V = V_2 - V_1$ is produced. Finally, the product $\Delta V' = \gamma \times \Delta V$ thus derived is compared with the judgement standard upper and lower limits U.L. and L.L.

When the particle concentration is larger than the standard value, a large number of particles are collected in the center portion 5 and therefore, the difference $\Delta V$ becomes larger. At the same time a large number of particles are deposited on the flat portion 3 and thus, the output signal $V_3$ from the light receiving element 21 becomes smaller than the standard value $V_{30}$. Therefore, the coefficient $\gamma$ becomes smaller than unity ($\gamma < 1$) and thus the product $\Delta V' = \gamma \times \Delta V$ becomes near the standard value of $\Delta V$. Contrary to this, when the particle concentration is too small, although the difference $\Delta V$ becomes smaller than the standard value, the product $\Delta V'$ becomes near the standard value of $\Delta V$, because the signal $V_3$ becomes large and the coefficient $\gamma$ becomes larger than unity.

In this manner, by utilizing the output signal $V_3$ from the third light receiving element 21 which receives the image on the flat portion 3, it is possible to compensate the variation of the particle concentration and/or particle amount and thus, the accurate judgement can be carried out without being affected by said variation.

EXAMPLE 3

This example is a hybrid method between the above mentioned two examples. That is to say, the output signal $V_3$ is first compared with the upper and lower reference values $DR_1$ and $DR_2$, and when $V_3 > DR_1$ or $V_3 < DR_2$, the product $\Delta V'$ is used for judgement. But, when $DR_1 \geq V_3 \geq DR_2$, $\Delta V$ is used for determining the particle pattern.

The present invention is not limited to the embodiments explained above, but may be modified in various ways. For instance, in the above embodiment, the image of the bottom surface of the reaction vessel is formed on the light detector, but it is also possible to receive separately the light fluxes passing through the flat portion, inclined portion and lowermost center portion. Further, in the above embodiment the inclined portion is formed conically, but may be shaped in any other forms such as pyramid, triangular prism and sphere. Moreover, the display device may be replaced by a printer.

According to the invention, since the reaction vessel comprises the flat portion on which particles are deposited corresponding to the particle concentration and/or particle amount and the inclined portion for forming the particle pattern corresponding to the agglutination reaction and the particle pattern on the flat portion is utilized to correct or compensate the variation in the particle amount and/or particle concentration, it is possible to effect the judgement in a precise manner.

What is claimed is:

1. A method of judging whether or not a particle agglutination reaction has occurred by detecting a particle pattern formed on a bottom surface of a reaction vessel containing a test liquid undergoing agglutination testing, comprising:
   photoelectrically detecting a particle pattern formed on a flat substantially horizontal portion of the bottom surface of said reaction vessel to produce a first signal representing at least one of an amount of particles and a concentration of particles contained in the test liquid, said flat substantially horizontal portion of the bottom surface being positioned above and surrounding a centrally located inclined portion of the bottom surface;
   photoelectrically detecting a particle pattern formed by particles decending upon said centrally located inclined portion of the bottom surface of said reaction vessel to produce a second signal representing the particle pattern of the test liquid; and
   when said first signal is within predetermined upper and lower values, judging whether or not a particle agglutination reaction has occurred on the basis of said second signal, and when said first signal is outside said predetermined upper and lower values, judging whether or not a particle agglutination reaction has occurred on the basis of a corrected second signal, with the correction thereto being a function of the first signal.

2. A method according to claim 1, wherein when said first signal is within predetermined upper and lower values, the occurrence of a particle agglutination reaction is judged by comparing the second signal with standard values.

3. A method according to claim 1, wherein when said first signal is outside said predetermined upper and lower values a coefficient for correcting a variation in at least one of the particle concentration and the particle amount is calculated from said first signal, and said second signal is multiplied by said coefficient to produce said corrected second signal, and wherein the occurrence of a particle aggulatination reaction is judged by comparing said corrected second signal with standard values.

4. A method according to claim 3, wherein said coefficient is derived by dividing said first signal by a standard value of the first signal which is obtained when at least one of the particle concentration and the particle amount are within a predetermined standard range.

5. A method according to claim 1, wherein said second signal is generated by deriving a difference between the particle pattern formed on a lower portion and a middle portion of said centrally located inclined portion.

6. A method according to claim 5, wherein an image of the particle pattern on said flat substantially horizontal portion is formed on a first light receiving element and said first signal is produced by said first light receiving element.

7. A method according to claim 6, wherein an image of the particle pattern formed on said lower portion and said middle portion of said inclined portion are projected on second and third light receiving elements, respectively, each producing a photoelectrically converted output, and wherein said second signal is produced by deriving a difference between the photoelectrically converted outputs.

8. A method according to claim 5, wherein a light flux transmitted through said flat substantially horizontal portion is received by a first light receiving element to produce said first signal.

9. A method according to claim 8, wherein light fluxes transmitted through said lower portion and said middle portion of said inclined portion are separately received by second and third light receiving elements, respectively, each producing a photoelectrically converted output and wherein said second signal is produced by deriving a difference between the photoelectrically converted outputs.

* * * * *